(12) United States Patent
Tautenhahn et al.

(10) Patent No.: US 10,878,944 B2
(45) Date of Patent: Dec. 29, 2020

(54) METHODS FOR COMBINING PREDICTED AND OBSERVED MASS SPECTRAL FRAGMENTATION DATA

(71) Applicants: Thermo Finnigan LLC, San Jose, CA (US); HighChem Ltd., Bratislava (SK)

(72) Inventors: Ralf Tautenhahn, Mountain View, CA (US); Timothy J. Stratton, Austin, TX (US); Robert Mistrik, Bratislava (SK)

(73) Assignees: Thermo Finnigan LLC, San Jose, CA (US); HighChem Ltd., Bratislava (SK)

( * ) Notice: Subject to any disclaimer, the term of this patent is extended or adjusted under 35 U.S.C. 154(b) by 302 days.

(21) Appl. No.: 15/934,936

(22) Filed: Mar. 23, 2018

(65) Prior Publication Data
US 2019/0294756 A1 Sep. 26, 2019

(51) Int. Cl.
*H01J 49/00* (2006.01)
*G16C 20/30* (2019.01)
(Continued)

(52) U.S. Cl.
CPC ............ *G16C 20/30* (2019.02); *G16C 10/00* (2019.02); *G16C 20/20* (2019.02); *G16C 20/40* (2019.02); *H01J 49/0036* (2013.01)

(58) Field of Classification Search
CPC ........ G16C 20/30; G16C 20/40; G16C 20/20; G16C 10/00; H01J 49/0036
See application file for complete search history.

(56) References Cited

U.S. PATENT DOCUMENTS

| 5,538,897 A | 7/1996 | Yates, III et al. |
| 8,639,447 B2 * | 1/2014 | Kim ................... G16B 5/00 |
| | | 702/19 |

(Continued)

FOREIGN PATENT DOCUMENTS

| CN | 101871945 A | 10/2010 |
| EP | 3002696 A1 | 4/2016 |
| WO | 2015/186012 A1 | 12/2015 |

OTHER PUBLICATIONS

Ausloos et al., "The Critical Evaluation of a ComprehensiveMass Spectral Library", J Am Soc Mass Spectrum 1999, 10, pp. 287-299.
(Continued)

*Primary Examiner* — Mohammad K Islam
(74) *Attorney, Agent, or Firm* — Thomas F. Cooney

(57) ABSTRACT

A method for generating a searchable small-molecule tandem mass spectrometry library comprises: (a) generating, by theoretical calculation and for each of a plurality of small-molecule compounds, a list of ion species, including fragment-ion species that are predicted, by the theoretical calculations, to be generated by tandem mass spectrometry (MS$^n$) analyses, where n≥2; (b) comparing at least a subset of the predicted ion species to entries in a database that includes a list of experimentally observed ion species; (c) matching a predicted mass-to-charge ratio (m/z) value of each of one or more of the predicted fragment-ion species to a respective experimentally measured m/z value of an experimentally observed fragment-ion species for which information is tabulated in the database; and (d) updating the predicted list of ion species based on information derived from the matched predicted and experimentally measured m/z values.

19 Claims, 5 Drawing Sheets

(51) Int. Cl.
*G16C 10/00* (2019.01)
*G16C 20/20* (2019.01)
*G16C 20/40* (2019.01)

(56) References Cited

U.S. PATENT DOCUMENTS

| | | | |
|---|---|---|---|
| 9,842,198 B2 | 12/2017 | Magarvey et al. | |
| 10,132,777 B2* | 11/2018 | Clowers | G01N 27/622 |
| 10,163,619 B2* | 12/2018 | Brown | H01J 49/004 |
| 10,393,752 B2* | 8/2019 | Rychnovsky | G01N 33/6848 |
| 2014/0138537 A1 | 5/2014 | Grothe, Jr. et al. | |
| 2015/0160231 A1* | 6/2015 | Meitei | H01J 49/0036 |
| | | | 702/22 |
| 2015/0262800 A1* | 9/2015 | Sugawara | H01J 49/4215 |
| | | | 250/252.1 |
| 2018/0166265 A1* | 6/2018 | Geromanos | G01N 30/8675 |
| 2018/0239863 A1* | 8/2018 | Erbilgin | G01N 33/00 |
| 2019/0018928 A1* | 1/2019 | Valkenborg | C12Q 1/6872 |

OTHER PUBLICATIONS

Heinonen et al., "Ab Initio Prediction of Molecular Fragments from Tandem Mass Spectrometry Data", German Conference on Bioinformatics GCB (2006), Dept of Computer Science, University of Helsinki, FI, GI-Edition: Lecture notes in informatics. Proceedings. ISSN/ISBN 16175468, 14 pages.

Hummel et al., "ProMEX: a mass spectral reference database for proteins and protein phosphorylation sites", BMC Bioinformatics 2007, 8:216, 8 pages.

Kind et al., "Identification of small molecules using accurate mass MS/MS search", Mass Spec Rev. 2018, 37, pp. 513-532.

Scheubert et al., "Computational mass spectrometry for small molecules", Journal of Cheminformatics 2013, 5:12, 24 pages.

Ridder et al., "Automatic Compound Annotation from Mass Spectrometry Data Using MAGMa", Mass Spectrometry (Tokyo), 2014, vol. 3 (Spec Iss 2), S0033, pp. 1-7.

Sheldon et al., "Determination of Ion Structures in Structurally Related Compounds Using Precursor Ion Fingerprinting", J Am Soc Mass Spectrom 2009, 20, pp. 370-376.

Wolf et al., "In silico fragmentation for computer assisted identification of metabolite mass spectra," BMC Bioinformatics 2010, 11:148, pp. 1-12.

Hufsky et al., "Computational mass spectrometry for small-molecule fragmentation", Trends in Analytical Chemistry 53 (2013), pp. 41-48.

Milman, "General principles of identification by mass spectrometry", Trends in Analytical Chemistry 69 (2015), pp. 24-33.

Yang et al., "Extending a Tandem Mass Spectral Library to Include MS2 Spectra of Fragment Ions Produced In-Source and MSn Spectra", J. Am. Soc. Mass Spectrom. (2017), vol. 28 (11), pp. 2280-2287.

* cited by examiner

METHODS FOR COMBINING PREDICTED AND OBSERVED MASS SPECTRAL FRAGMENTATION DATA

TECHNICAL FIELD

The present invention relates to mass spectrometry of small molecules and, more particularly, to methods for constructing and utilizing tables of ion fragmentation pathways for use in identification of small molecules.

BACKGROUND OF THE INVENTION

In various of the biological sciences, so-called "small molecules" are non-polymeric biologically active organic molecules of molecular weight less than about 2000 Da. This definition excludes many nucleic acids, proteins and polysaccharides but does apply to individual amino acids, peptides simple sugars and some simple oligomers. One particularly important class of small molecules, from a medical standpoint, are the various drug compounds and their metabolites. The field of metabolomics is concerned with metabolite profiling and, especially, with the differential study of the metabolome between experimental and control groups when challenged with an external stimulus (Nicholson J, Connelly J, Lindon J, et al. Metabolomics: a platform for studying drug toxicity and gene function. Nat Rev Drug Discov 2002, 1, 153-161). The metabolome is defined as the complete set of small molecule endogenous metabolites, intermediates and metabolism products found in an organism. It can provide an instantaneous snapshot of the entire physiology of a living being. With its potential to provide a comprehensive snapshot of the biochemistry of a biological system, metabolomics can be used for life science research in areas such as disease and biomarker discovery. Metabolomics can also be combined with genomics, transcriptomics and proteomics studies, which are also known as multi-omics, to provide comprehensive insights into biological processes. such as a drug treatment, a biochemical or environmental stress, or pathologies such as mutant/resistance-bred organisms. The stimulus could also be non-biological, such as food processing; as a consequence, metabolomics has huge potential across several application areas, including food and nutrition. Because metabolomics aims to comprehensively identify and measure a large number of compounds in complex mixtures, its goals are a challenge for standard analytical chemistry. As a result, mass spectrometry has emerged as an alternative to NMR-based metabolomics, offers high selectivity and sensitivity, and has the potential to assess metabolites in both a qualitative and quantitative manner.

In general, mass spectrometric structural elucidation of ionized bio-molecules or other organic molecules of complex or moderately complex structure, is often carried out using a tandem mass spectrometer that is coupled to a chromatograph. The general techniques of conducting mass spectrometry (MS) analysis of ions generated from compounds separated by chromatography (e.g., liquid chromatography (LC), gas chromatography (GC) ion chromatography (IC), etc.) are referred to by acronyms such as "LC-MS", "GC-MS", "IC-MS", etc. In such studies, a chromatograph is used to effect at least partial separation of an initial mixture of organic molecules into separate fractions, and a mass spectrometer is utilized in an attempt to identify and/or quantify the organic molecules in each fraction. The most basic type of information that is provided by a mass spectrometer is a list of the mass-to-charge ratios (m/z) of the ions that are present in the analyzed fraction. However, the charge states of ions can sometimes be readily discerned, especially if electrospray ionization (ESI) is employed to ionize molecules present in a liquid chromatography fraction. In such instances, the m/z measurements may be readily converted to measurements of ion masses.

Because of the extensive range and variety of analytes and other organic compounds that may occur in a biologically-derived sample, a simple measurement of m/z or even ion mass generally insufficient to uniquely identify or characterize such an organic compound, unless either the compound is of extremely simple or well-known structure or else the sample is of low complexity (e.g., highly purified). Thus, in almost all instances, an initially-generated ion (i.e., a precursor ion) must be broken down into smaller fragments or moieties which may be more readily recognized, either because the fragments or moieties are themselves well-known or well-characterized or else because the pattern of fragment or moiety generation from the particular m/z of the precursor is itself well-known or well-characterized. The general process of selecting and isolating a precursor ion, fragmenting the precursor ion to form fragment ions and subsequently mass analyzing the fragment ions is known as "tandem mass spectrometry".

In the simplest form of tandem mass spectrometry experiment, known as an "MS/MS" or, alternatively, "MS$^2$" experiment, a "full-scan" mass spectrum, which is an initial survey of the ions present in the ionized sample, is obtained. This initial mass spectrum is frequently referred to as an "MS$^1$" mass spectrum. Subsequently, one or more ion species of particular selected m/z values are isolated (that is, purified by expulsion of other ions), often but not necessarily sequentially; the isolated ions are fragmented; and the fragment ions are mass analyzed. This sequence of events may be iterated. Specifically, an "iteration" is the selection and isolation of particular fragment-ion species, these selected and isolated fragment ions thus becoming a new generation of precursor ions, and further fragmentation of the so-isolated fragments followed by mass analysis of the resulting product ions. The process of fragmenting earlier first-generation fragments and mass analyzing the resulting second-generation fragment ions is often referred to as an "MS$^3$" experiment. Similarly, the second-generation fragments may themselves be fragmented to generate even smaller fragment ions and so on. In the general case, a mass spectrum obtained after (n−1) iterated stages of selection and fragmentation may be referred to as an "MS$^n$" spectrum. Given the sensitivity of modern mass spectrometers, this process may be repeated many times over. For example, the inventors have routinely obtained "MS$^9$" spectra over the course of development of the present invention.

A product-ion mass spectrum will exhibit a set of fragmentation peaks (a fragment set) which, in many instances, may be used as a means to derive structural information relating to the original molecule from which the originally isolated first-formed precursor ions were generated. In the general study of polypeptides and protein molecules, the loci of bond breakage, generally along a polymeric backbone, that results in fragment-ion formation is reasonably well understood under certain controlled fragmentation conditions. Thus, the types of fragments that may be generated under the application of such controlled conditions may be readily predicted and, as a result, basic MS$^2$ experiments may be sufficient to identify or characterize various protein or polypeptide analytes in terms of their amino acid sequences. Accordingly, tandem mass spectrometry is employed extensively in the field of so-called "top-down"

proteomics. Unfortunately, unlike polypeptides and proteins, the fragmentation patterns for metabolites and other small molecules cannot be readily predicted. Therefore, as one approach to address this issue, databases, such as "mzCloud" (www.mzCloud.org) and "METLIN", of mass spectra of known small molecule compounds have been and continue to be developed. Thus, provided that the required information is available in a database of this sort, a researcher or analyst can hypothetically identify a metabolite analyte by recognizing a match between an experimental measurement of the fragmentation pattern of the analyte and a database entry. Unfortunately, although these databases contain information relating to tandem mass spectral results of a large number (2000-5000) of small molecule compounds, the total number of compounds which are of potential interest (for example, an estimated 200,000 metabolites) is significantly greater. Thus, there is at least a 95% probability that any given metabolite will not have a corresponding entry in the database.

In an attempt to overcome the existing limitations of small-molecule tandem-mass-spectral databases (where the term "small molecule" as used here and in the subsequent text is as defined above), various in-silico approaches have been developed (Sheldon M T, Mistrik R, Croley T R, Determination of Ion Structures in Structurally Related Compounds Using Precursor Ion Fingerprinting, J Am Soc Mass Spectrom 2009, 20, 370-376; Ridder L, van der Hooft, J J J, Verhoeven, S, Mass Spectrom (Tokyo) 2014, 3, Spec Iss 2:S0033). These algorithmic approaches, which are embodied in software packages, such as MassFrontier, MetFrag and MAGMA, attempt to calculate all conceivable fragmentation pathways, within certain constraints, starting from a known or hypothesized chemical structure and using various fragmentation rules or bond-energy constraints values taken from literature. Because of a distribution of bond-energy values within any reasonable structure, the calculated fragmentation patterns are dependent on the applied fragmentation energy, which is a controllable experimental parameter and an adjustable parameter within the algorithms.

The results of each such in-silico calculation, is a tree-like data structure, such as is schematically illustrated in FIG. 1A, for each value of the adjustable fragmentation energy parameter. Each calculated hypothetical mass spectrum comprises a node (each such node illustrated as a box in FIG. 1A) wherein the nodes are organized into levels, where each level corresponds to a different generation of fragment ions (each generation corresponding to a respective value of the variable, n, in "MS$^n$"). For example, in the hypothetical fragmentation tree 10 that is schematically illustrated in FIG. 1A, the node 1 on the top level of the tree corresponds to a precursor-ion spectrum consisting of just three mass spectral lines and each of the nodes 2.1, 2.2 and 2.3 on the second level corresponds to a respective predicted MS$^2$ mass spectrum as might result from fragmentation of a one of the three ion species indicated in node 1. Likewise, each of the nodes 3.1-3.9 on the third level of the tree schematically represents a predicted MS$^3$ mass spectrum as might result from fragmentation of a respective one of the nine ion species indicated in the second-level nodes 2.1-2.3. Similarly, the fourth level of the tree, as illustrated, consists of twenty-seven predicted MS$^4$ mass spectra (nodes 4.1-4.27, not all of which are labeled in order to avoid a confusion of lines) as might be generated by fragmentation of a respective one of the twenty-seven ion species indicated in the third level nodes.

In this document, the term "fragmentation pathway" refers to a sequence of fragmentation events, wherein the first such fragmentation event is the fragmentation of a single unique precursor ion species and each subsequent fragmentation event is the fragmentation of a single unique existing fragment ion generated in a previous fragmentation event of the sequence. This definition is not intended to preclude simultaneous fragmentation of a plurality of precursor-ion (or previously-generated fragment-ion) species. If two ion species are fragmented simultaneously, then the two ions correspond to different respective fragmentation pathways. If a single precursor ion (or previously-generated fragment ion) yields, upon fragmentation, a plurality of new fragment-ion species, then each such new fragment-ion species corresponds to a different respective fragmentation pathway. After a number of such fragmentation events, a fragmentation pathway ends with the generation of a penultimate product-ion species. (It should be noted that ions that only differ by one or more isotopic substitutions or isotopic variations are considered to belong to the same ion species.) As an example, the partial tree structure 20 shown in FIG. 1B illustrates a selected portion of the tree 10 of FIG. 1A that corresponds to a single fragmentation pathway. The individual precursor, fragment and product ions that correspond to the single illustrated fragmentation pathway are denoted by a star symbol in FIG. 1B. Accordingly, the illustrated fragmentation pathway commences by a fragmentation event 21 in which the intermediate-m/z precursor ion that is denoted by a star above node 1 is fragmented so as to generate the three first-generation fragment ions illustrated by vertical lines at node 2.2. The second fragmentation event 22 of the illustrated fragmentation pathway is the fragmentation of the highest-m/z (rightmost) first-generation fragment-ion species denoted by a star above node 2.2. This second fragmentation event generates the three second-generation fragment ions depicted by vertical lines at node 3.6. Finally, the third fragmentation event 23 in the sequence generates the final product ion depicted by the leftmost vertical line at node 4.16 and denoted by a star. Each of the three ion species at node 4.16 represents a termination of a different respective ion pathway, as shown in FIG. 1A. With three lines per mass spectrum, as illustrated in FIG. 1A, the twenty-seven fourth level nodes 4.1-4.27 corresponds eighty-one different unique fragmentation pathways. In actual practice, however, each fragment-ion mass spectrum may comprise many more than just three lines. Further, several such tree data structures (each corresponding to a different value of the fragmentation energy parameter) may be calculated for each starting chemical structure.

Each of the in-silico approaches includes a scoring routine which attempts to find, within the set of calculated fragment spectra, a set of closest matches to an observed fragmentation pattern. These approaches are useful when a user or analyst is conducting a targeted experiment in order to obtain a simple true-vs-false answer to the question of whether the particular targeted analyte is present in a sample. In cases where multiple structures must be considered, these methods can only generate a ranking based on e.g., the number of observed fragments that can be explained by the in silico fragmentation. These methods cannot be used to identify unknown metabolites (i.e., metabolites where the structure is unknown) because, in the absence of meaningful constraints on the total number of calculable fragmentation pathways, the resulting overwhelming number of such pathways is virtually guaranteed to result in many false-positive identifications. False-positive identifications and false-negative identification failures also arise by virtue of the fact that not all predicted fragment ions are actually present in real mass spectra. Thus, at best, these methods can only be used to correlate an observed fragmentation spectrum with the known structure of a potential precursor ion. Thus, the field of untargeted metabolomics study is presently limited by the difficulties of compound identification. The present invention addresses a need for a solution to these difficulties.

BRIEF SUMMARY

The present disclosure teaches methods that combine predicted (in silico) fragmentation results obtained through software (such as MassFrontier) with actual measured $MS^n$ fragmentation data from obtained from a mass spectral database (such as mzCloud). The combined results are formulated into a new type of spectral Tree data structure, herein termed a TR-tree, which combines theoretically calculated fragmentation results with experimentally observed data by searching for matches between predicted and observed ions and fragmentation pathways and updating the tree structure by marking matched fragmentation pathways as verified and by deleting or otherwise marking as invalid other non-observed fragment ions or fragmentation pathways. Further, the matches may be employed to annotate the database of experimentally observed data with species assignment information that is imported from the matched theoretically calculated results.

According to a first aspect of the present teachings, a method for generating a searchable small-molecule tandem mass spectrometry library is provided, the method comprising: (a) generating, by theoretical calculation and for each of a plurality of small-molecule compounds, a list of ion species, including fragment-ion species that are predicted, by the theoretical calculations, to be generated by tandem mass spectrometry ($MS^n$) analyses, where $n \geq 2$; (b) comparing at least a subset of the predicted ion species to entries in a database that includes a list of experimentally observed ion species; (c) matching a predicted mass-to-charge ratio (m/z) value of each of one or more of the predicted fragment-ion species to a respective experimentally measured m/z value of an experimentally observed fragment-ion species for which information is tabulated in the database; and (d) updating the predicted list of ion species based on information derived from the matched predicted and experimentally measured m/z values.

According to another aspect of the present teachings, a method for generating a searchable small-molecule tandem mass spectrometry library is provided, said method comprising: (a) generating, by theoretical calculation and for each of a plurality of small-molecule compounds, a list of predicted ion species, each said list including a predicted precursor-ion species and a corresponding list of fragment-ion species that are predicted, by the theoretical calculations, to be generated by fragmentation of the respective precursor-ion species; (b) comparing at least a subset of the predicted precursor-ion species and predicted fragment ion species to entries in a database that includes a list of experimentally observed precursor-ion species and that further includes, for each of said experimentally observed precursor-ion species, a list of fragment-ion species that are experimentally observed to be generated by fragmentation of the respective precursor-ion species; (c) matching a pair of predicted ion species, said pair comprising a predicted precursor-ion species and a predicted corresponding fragment ion species to a pair of experimentally observed ion species comprising an experimentally observed precursor ion species and a corresponding experimentally observed fragment-ion species; (d) identifying at least one other predicted fragment-ion species in the list of predicted fragment-ion species corresponding to the matched precursor-ion species for which there is no match in the list of experimentally observed fragment-ion species that correspond to the matched experimentally observed fragment ion species; and (e) updating the predicted list of ion species by deleting or otherwise marking as invalid the entry or entries corresponding to the at least one other predicted fragment-ion species.

In this document, the term "database" refers to a collection of experimentally determined mass spectrometry data comprising at least a list of experimentally observed mass-to-charge ratio (m/z) values for each of a plurality of mass analyzed compounds. As used in this document, the term library refers to a searchable collection of mass spectrometry information that comprising at least a list of mass-to-charge ratio (m/z) values for each of a plurality of compounds, where the collection may a database, as defined above, or, alternatively, the collection may include, in the list or lists of m/z values, at least some m/z values that have been predicted my means of calculation and that have not been experimentally verified. Generally, a library or database will be designed to be searchable for the purpose of permitting an analyst to attempt to determine or verify the identity of a small-molecule analyte within a sample by comparison of experimentally determined m/z values derived by mass analysis of the sample to various of the m/z values tabulated in the database or library.

In this document, the term "tandem mass spectrometry" is used in a broad sense to refer to any number of fragmentation iterations and the term "product ions" is used synonymously with "fragment ions". When one generation of fragment ions is further fragmented so as to generate a subsequent generation of fragment ions, then the earlier generation of fragment ions may also be referred to as "precursor ions" with respect to the subsequent fragmentation stage. Thus, in this document, the terms "first generation precursor ions" and "first generation precursor ion species" are employed to identify precursor ions that are delivered to a mass analyzer from an ion source, without a prior fragmentation stage. The terms "precursor ions" and "precursor ion species" are used, in this document, in a general sense to refer to either first generation precursor ions or to those precursor ions that are also "fragment ions".

Many different techniques of ion fragmentation are known. These include, without limitation, collision-induced dissociation (CID), electron-capture dissociation (ECD), electron-transfer dissociation (ETD), photodissociation including infrared multiphoton dissociation (IRMPD), surface-induced dissociation (SID), and higher-energy dissociation (HCD). Fragmentation generally proceeds by supplying energy to a polyatomic ion. If the supplied energy is directed to or becomes localized at a particular chemical bond within the polyatomic ion and the localized energy is greater than the bond energy, then there will be a non-zero probability that the bond will break, thereby forming fragments. The types of fragments that are formed depends on the type of fragmentation technique employed as well as the applied fragmentation energy. As is known, each fragmentation technique is associated with a respective method for controlling the applied energy. The original charge may be distributed among the fragments or may be limited to only one or some of the fragments. Only charged fragments may be detected by mass spectrometry; neutral fragments are not detected. The methods of the present teachings are not limited to any particular ion fragmentation technique. However, when comparing experimentally observed fragmentation data to theoretically predicted fragmentation results or when comparing experimentally observed fragmentation data to tabulated fragmentation data in a database or in a mass spectral library or when comparing databases or libraries, it will generally be the case that such comparisons will be limited to between similar fragmentation techniques and similar applied fragmentation energies.

BRIEF DESCRIPTION OF THE DRAWINGS

To further clarify the above and other advantages and features of the present disclosure, a more particular description of the disclosure will be rendered by reference to specific embodiments thereof, which are illustrated in the appended drawings. It is appreciated that these drawings depict only illustrated embodiments of the disclosure and are therefore not to be considered limiting of its scope. The disclosure will be described and explained with additional specificity and detail through the use of the accompanying drawings, not necessarily drawn to scale, in which.

DETAILED DESCRIPTION

The present disclosure describes novel methods for constructing and utilizing tables of ion fragmentation pathways for use in identification of small molecules. The following description is presented to enable any person skilled in the art to make and use the invention, and is provided in the context of a particular application and its requirements. Various modifications to the described embodiments will be readily apparent to those skilled in the art and the generic principles herein may be applied to other embodiments. Thus, the present invention is not intended to be limited to the embodiments and examples shown but is to be accorded the widest possible scope in accordance with the features and principles shown and described.

If an $MS^n$ mass spectral experiment is performed with a sufficiently large value of n and under controlled applied fragmentation energy utilizing a "soft" fragmentation technique, such as collision-induced ionization (CID) or even higher energy collisional dissociation (HCD), then, at some value of n, the observed fragment-ion mass spectra will consist largely of some form of relatively small "chemical building block" moieties which resist further fragmentation, at least at the applied fragmentation energy. Let this particular value of n be denoted as no and let the corresponding level of fragmentation be denoted as $MS^{n_0}$. Note that $n_0$ is a function of the applied fragmentation energy, $E_f$. These relatively small sub-structure moieties will, in many cases, be well-known or readily identifiable. If a fragmentation survey program is undertaken whereby a large number of such tandem mass spectral experiments are performed on standard or otherwise characterized chemical compounds covering a wide range of chemical compositions of interest to a particular field of study (e.g., metabolomics), then the mass spectral signatures of most of the important or relevant sub-structure moieties should be represented in the fragmentation data, regardless of whether or not the sub-structure moieties are identifiable.

Figure 2A:
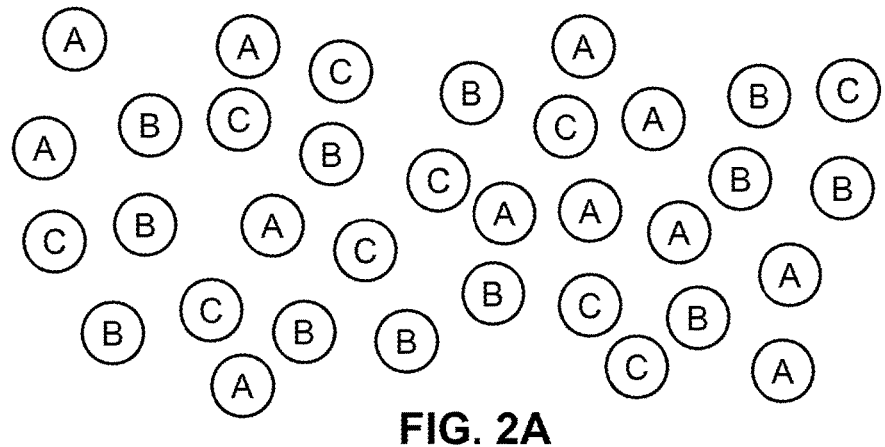
FIG. 2A is a schematic depiction of a hypothetical mixture of fragment ions mostly composed of fundamental building-block chemical moieties subsequent to a final stage of repeated fragmentation.
Figure 2B:
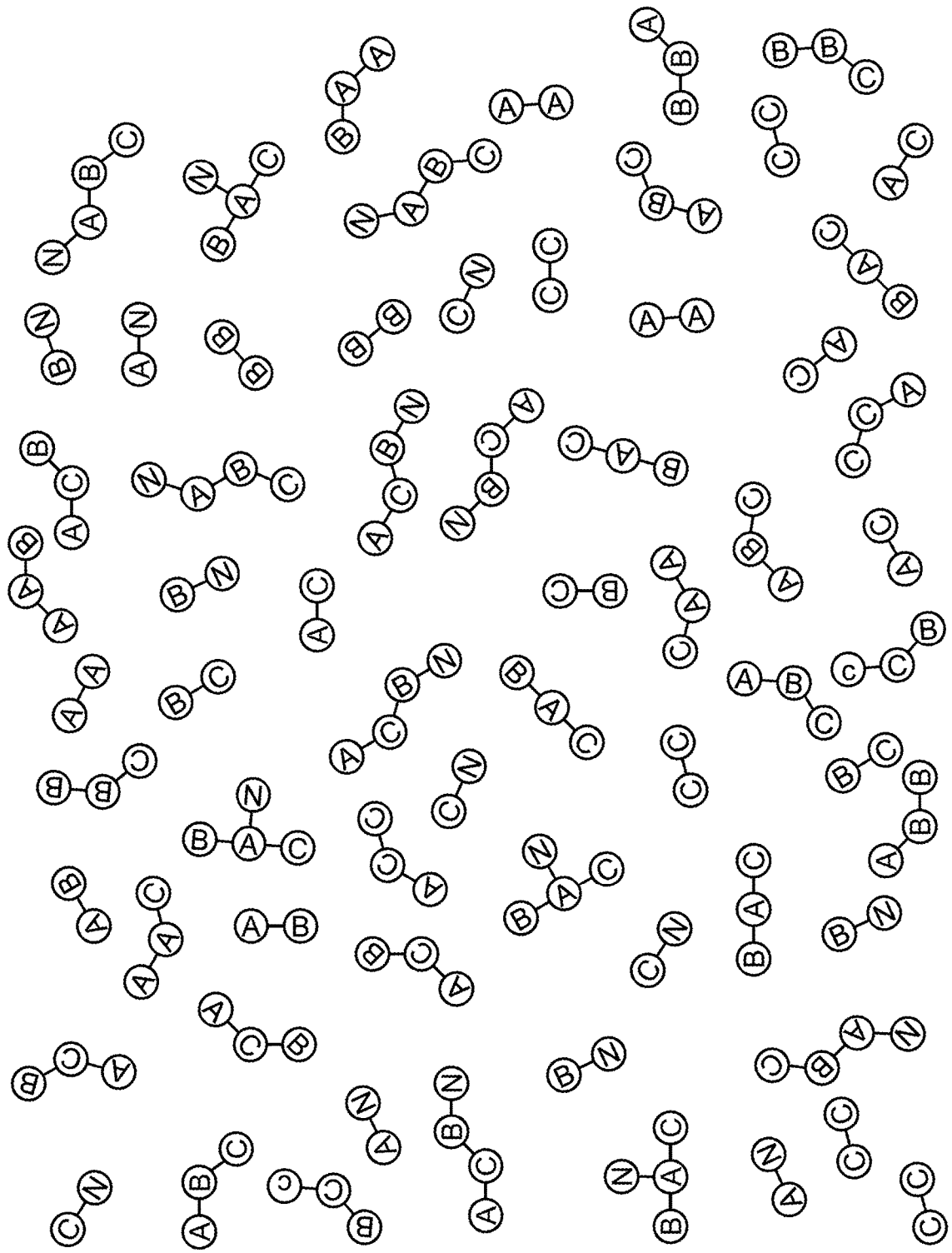
FIG. 2B is a schematic depiction of a hypothetical mixture of fragment ions mostly composed of bonded building-block chemical moieties prior to a final stage of repeated fragmentation.

As an example, assume that one such compound for which fragmentation data is available comprises the chemical components "A", "B" and "C" which are stable against fragmentation at an applied fragmentation energy, $E_{f1}$. Then, the sample of fragment ion species at the $n_0(E_{f1})$ level of fragmentation would be expected to mostly consist of the individual "A", "B" and "C" ionized moieties, as illustrated in FIG. 2A. Working backwards from the maximum level, $n_0(E_{f1})$ of fragmentation (where $n_0(E_{f1})$ may vary from one compound to another at the same applied fragmentation energy, $E_{f1}$), then the fragment-ion spectra at slightly less values of n (e.g, $n_0-1$, $n_0-2$) are expected to comprise a mixture of ion species that resembles the mixture that is schematically depicted in FIG. 2B. It is expected that this mixture would comprise, for the most part, ion species whose structures are bonded combinations of at least some of the basic moieties "A", "B" and "C" possibly including additional ion species that further incorporate more additional chemical moieties, "N", that are lost as neutral polyatomic units at the final fragmentation step. Although FIG. 2B illustrates a variety of possible fragment ions that are bound combinations of the building-block moieties and neutrals (e.g., A-B, A-C, B-C, A-A, B-B, C-C, A-N, B-N, C-N), not all of these combinations should be expected to occur, since their appearance as fragments depends on whether they occur bound together in the structure of the parent molecule, compound X. Further, additional larger, more-complex fragments may also be present.

Further, the initial stages of fragmentation (e.g., $MS^2$, $MS^3$, etc.) of a standard or otherwise characterized compound are expected to yield some proportion of relatively large fragments (relative to the size of the initial known ion or ions generated by ionization of the compound) which may be identified on the basis of either their recognized complementary masses, recognized loss of neutral polyatomic units or recognized loss of basic building-block moieties as observed in mass spectra obtained at higher levels of fragmentation. Nonetheless, the assignments of some observed mass spectral peaks of fragment ions may remain uncertain or ambiguous. This uncertainty may be propagated forward to mass spectral data obtained from fragments generated from higher levels of fragmentation. Therefore, mass spectral fragmentation libraries are generally incomplete, both in terms of the number of compounds represented in such libraries as well as in terms of the assignments of chemical compositions to some experimentally observed peaks.

Whereas experimentally determined mass spectral libraries of fragmentation pathways are generally incomplete, the in silico calculated fragmentation trees are generally expected to include extraneous or inconsistent entries, since not all predicted fragments are actually observed in actual experiments or else are observed but at applied fragmentation energies that are inconsistent with the predictions. Such extraneous or inconsistent entries are expected to have adverse effects on the accuracy of searches against the information in the calculated fragmentation trees that are made for the purpose of matching observed fragmentation patterns of unknown compounds. Accordingly, the inventors of the present invention have recognized that the field of metabolomics and, more generally, the field of small molecule identification may be advanced by cross-referencing experimental fragmentation data to calculated fragmentation patterns and by updating both the calculated fragmentation trees and the observed experimental data based on the cross referencing. Such methods are further described below.

Figure 1A:
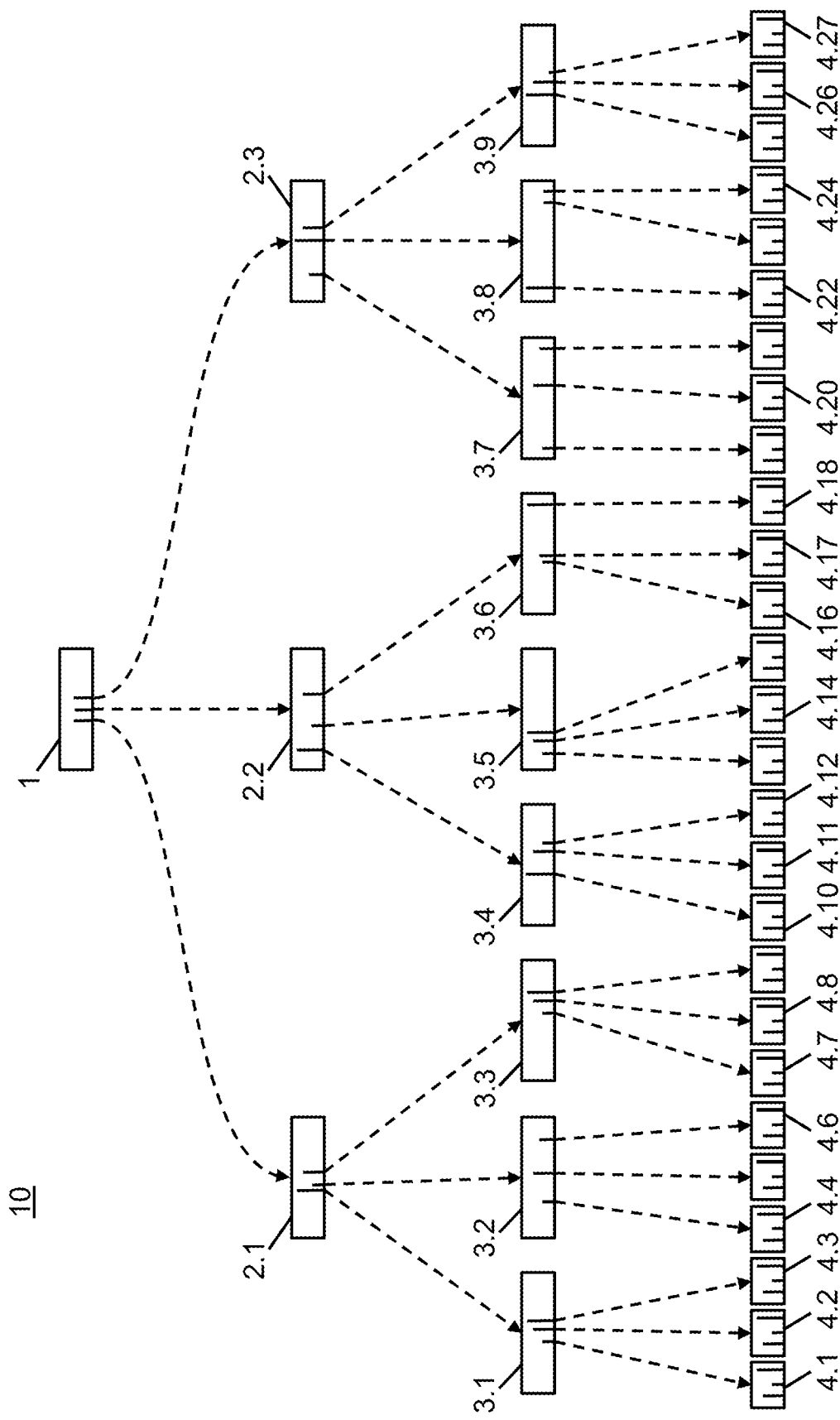
FIG. 1A is a schematic illustration of a node structure of a hypothetical in silico fragmentation calculation.
Figure 1B:
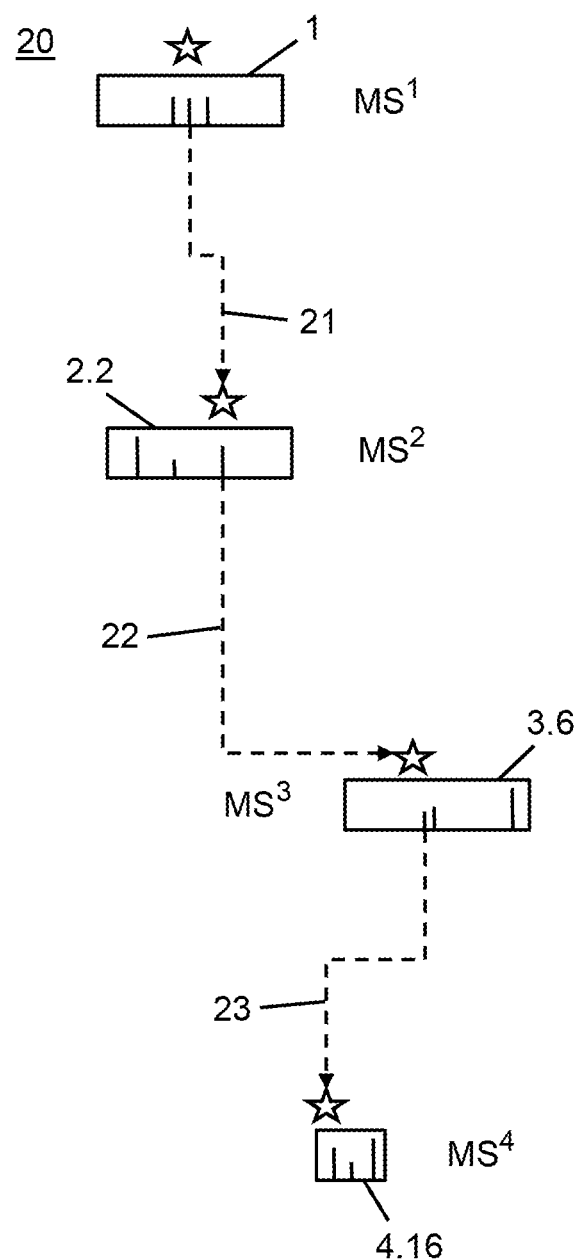
FIG. 1B is a selected portion of the schematic tree structure of FIG. 1A illustrating a single fragmentation pathway, as defined herein.
Figure 3:
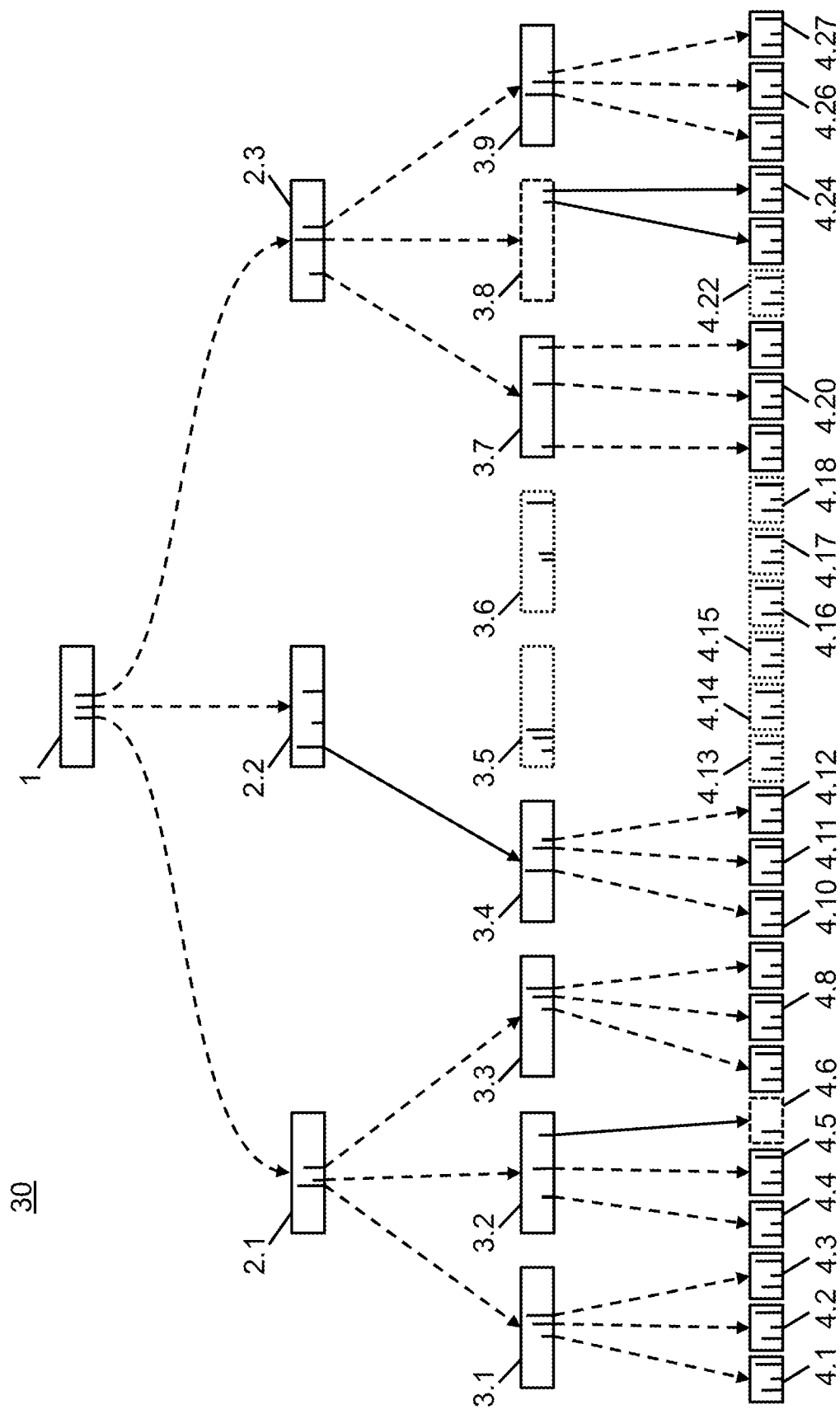
FIG. 3 is a schematic depiction of a curated hybrid fragmentation tree after updating with information from a database of experimental tandem mass spectral data obtained from standard or otherwise characterized or known compounds.

Assume, wholly for purposes of illustration, that the fragmentation tree structure 10 depicted in FIG. 1A represents a complete set of tentatively possible ion fragmentation pathways, as calculated by an in silico calculation method, of an ionized "compound X" for which no prior experimental tandem mass spectral data exists. Each one of the nodes below the top level node 1 (e.g., nodes 2.1-2.3, nodes 3.1-3.9 and nodes 4.1-4.27) is depicted, in FIG. 1A, by a box with lines that represent a hypothetical calculated fragment-ion mass spectrum, where m/z values increase from left to right across each box. Further assume, also for illustration purposes, that the tree structure 30 depicted in FIG. 3 represents a modified version of the tree structure 10 in which certain of the fragmentation pathways have been verified by actual mass spectral experiments on other compounds and certain other fragmentation pathways have been eliminated, as non-viable, based on those same experiments. For purposes of direct comparison, the applied fragmentation energy (or energies) utilized in the experiments should match the fragmentation energy (energies) that is assumed in the calculations. In the hypothetical tree structure 30 of FIG. 3, verified fragmentation results are indicated by solid-line arrows connecting nodes and eliminated pathways are indicated by dotted-line boxes and, in comparison to tree structure 10, the deletion of arrows and of un-observed mass spectral lines.

Still with reference to FIG. 3 and its comparison to FIG. 1A, assume, wholly for purposes of illustration, that controlled tandem mass spectral experiments of a different compound ("compound Y") have detected the fragment ion having the greatest m/z value in node 3.2 (i.e., the rightmost line depicted at node 3.2), which corresponds to an $MS^2$ mass spectrum of compound X. Assume, further, that those same controlled experiments indicate that further fragmentation of that detected ion yields only a single one of the predicted $MS^3$ ions, indicated as the single line at node 4.6 in FIG. 3. In this case, comparison of node 4.6 of FIG. 3 to node 4.6 of FIG. 1A indicates that, although the detected $MS^3$ ion was predicted by the in silico calculations, two other predicted $MS^3$ ions were not observed in the actual experiments. Therefore, the un-observed predicted $MS^3$ lines of node 4.6 (corresponding to respective fragmentation pathways) are deleted from (or, otherwise marked or annotated as non-viable) in the modified fragmentation tree 30. Simultaneously, chemical composition and/or structural information from the in-silico calculations relating to the matched ion peaks in nodes 3.2 and 4.6 can be used to update corresponding entries in a separate database relating to the experimental tandem mass spectra of compound Y. These updates of both the calculated fragmentation tree and the annotations of the experimental database are possible because the properties of the matched fragment ions are independent of the properties of both compound X and compound Y.

As another example and still with reference to FIG. 3 and its comparison to FIG. 1A, further assume, wholly for purposes of illustration, that controlled tandem mass spectral experiments of another compound ("compound Z") have detected the intermediate-m/z fragment ion depicted in node 2.3 of FIG. 1A and have also determined that, upon further fragmentation of this fragment ion, only the two highest-m/z predicted fragment ions (but not the lowest-m/z predicted fragment ion) of node 3.8 are experimentally detected. Accordingly, all three fragmentation pathways that terminate at node 4.22 of the modified hybrid fragmentation tree 30 are deleted or otherwise marked as non-viable. Simultaneously, chemical composition and/or structural information from the in-silico calculations relating to the matched ion peaks in nodes 2.3 and 3.8 can be used to update corresponding entries in a separate database relating to the experimental tandem mass spectra of compound Z.

As another example and still with reference to FIG. 3 and its comparison to FIG. 1A, further assume, wholly for purposes of illustration, that controlled tandem mass spectral experiments of another compound ("compound W") have detected the intermediate-m/z $MS^1$ precursor ion depicted in node 1 of FIG. 1A and, also, that upon fragmentation of this precursor ion, only the single leftmost (least m/z) predicted fragment ion species (but not the greater-m/z fragment ion species) of node 2.2 were experimentally detected. Accordingly, in this instance, all eighteen predicted fragmentation pathways that relate to further fragmentation of the predicted but un-observed fragment ions of node 2.2 30 are deleted or otherwise marked as non-viable in the hybrid fragmentation tree 30. This update of fragmentation tree 30 includes removal of nodes 3.5 and 3.6 and nodes 4.13-4.18 from further consideration in pattern search matches that utilize the hybrid tree. Simultaneously, chemical composition and/or structural information from the in-silico calculations relating to the matched ion peaks in node 1 and node 2.2 (one matching peak in each such node) can be used to update corresponding entries in a separate database relating to the experimental tandem mass spectra of the compound W.

Figure 4:
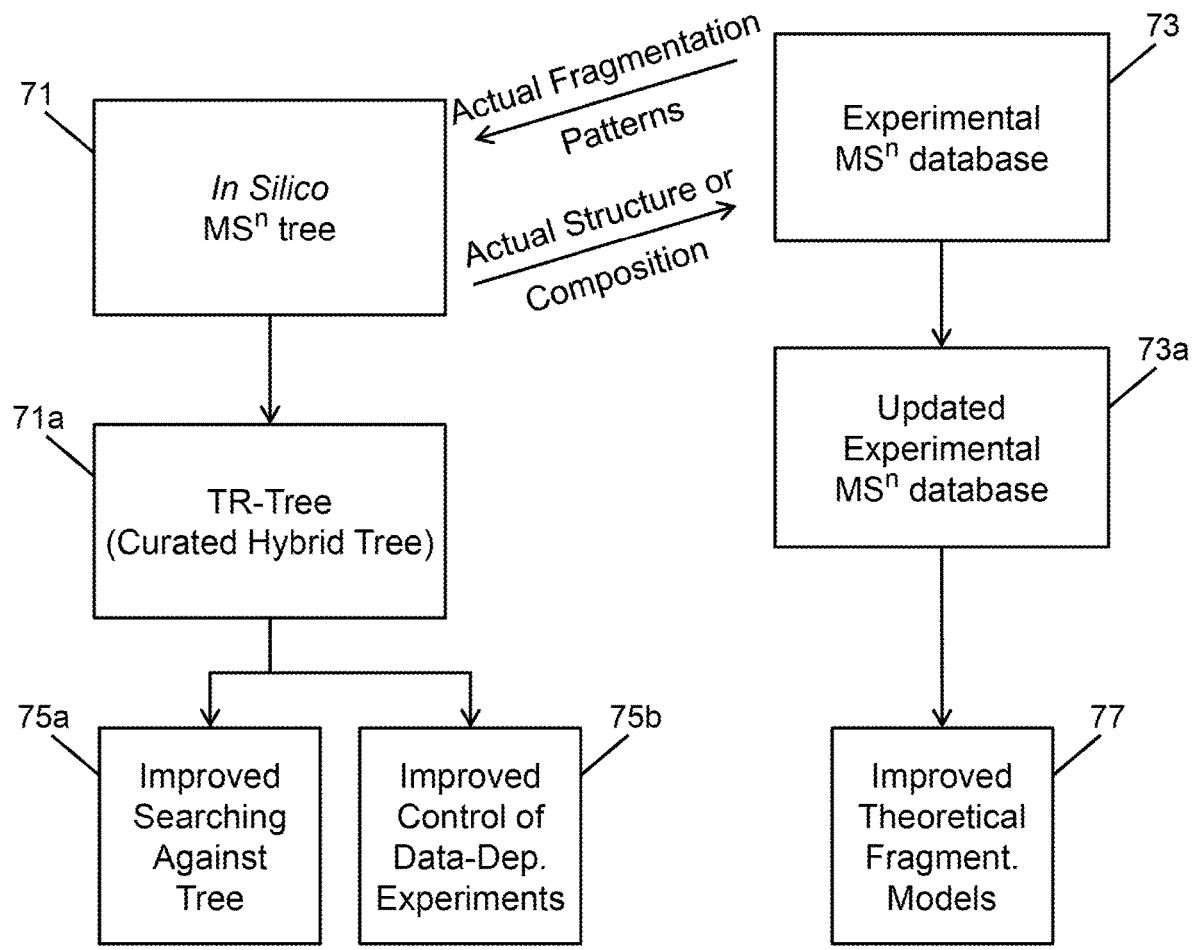
FIG. 4 is a schematic depiction of cross-referencing experimental fragmentation data in a database to an in silico calculated fragmentation tree and thereby updating both the database and the calculated fragmentation tree.

FIG. 4 schematically illustrates a general procedure of cross-referencing an in silico calculated fragmentation tree 71 (such as the hypothetical fragmentation tree 10 depicted in FIG. 1A) to a database 73 of $MS^n$ experimental data of a variety of standard or otherwise characterized or known compounds where the compounds are chosen to cover a wide range of chemical compositions and structures. The procedure is especially applicable to the study of metabolites in humans or animals but can be extended generally to the study of small molecules. By recognizing matches between observed and predicted ion fragmentation results and, further, by recognizing extraneous (not observed) predicted ion fragments, the purely computationally derived fragmentation tree 71 may be curated by validating certain of the predicted fragmentations and invalidating others, thereby updating the original fragmentation tree with the benefit of known information. The updated fragmentation tree 71a thus becomes a curated (or at least partially curated) fragmentation tree that is referred to here as a TR-tree, a hypothetical example of which is the TR-tree 30 depicted in FIG. 3. The TR-tree is a hybrid tree because it combines computational results with experimentally derived data.

Simultaneous with the updating of a computationally derived fragmentation tree 71 (or an updating of a previously updated TR-tree), the experimental database 73 may itself be updated or augmented by the importing of certain information derived from the computations into the database. By recognizing matches between observed and predicted ion fragmentation results, the actual chemical composition and possibly the structure of the matched fragments can be imported into the database 73 from the computationally derived fragmentation tree 71 thereby generating an updated experimental database 73*a*. The importation of this information is possible because every mass spectral line stored in the fragmentation tree 71 pertains to a particular fragment composition and/or structure by virtue of the manner by which the fragmentation tree is constructed. The so-transferred data may permit for assignment of previously un-assigned observed mass spectral lines in the updated database 73*a*.

The curated hybrid fragmentation tree 71*a* that is here referred to as a TR-tree may be employed for more reliable searching 75*a* of the fragmentation tree for fragmentation patterns that best match an observed fragmentation pattern of an unknown compound. The updating of the fragmentation tree improves this type of search process through the elimination of many irrelevant fragmentation pathways, thus reducing the incidence of false positive matches. Also, the improved-reliability fragmentation pathways stored in the TR-Tree 71*a* may be employed as input to an operating mass spectrometer instrument, while it is performing experiments, for the purpose of making automated real-time data dependent decisions 75*b* of which ion species to isolate and fragment so as to obtain the most informative data from the fragmentation results. Finally, the updated experimental database 73*a* having confirmed assignments of observed lines to fragment-ion compositions and structures may lead to the development of improved theoretical models 77 of the mechanisms and kinetics of fragmentation in metabolites and/or other small molecules so that unknown fragmentation patterns might be calculated and predicted from first principles.

The discussion included in this application is intended to serve as a basic description. Although the present invention has been described in accordance with the various embodiments shown and described, one of ordinary skill in the art will readily recognize that there could be variations to the embodiments without departing from the scope of the present invention as defined in the claims. The reader should be aware that the specific discussion may not explicitly describe all embodiments possible; many alternatives are implicit. Accordingly, many modifications may be made by one of ordinary skill in the art without departing from the scope of the invention and neither the description nor the terminology is intended to limit the scope of the invention. Any patents, patent publications or technical publications or technical documents mentioned within this disclosure are hereby incorporated by reference herein. If any statements in the mentioned documents should conflict with statements made in this application, then the present application will control.

What is claimed is:

1. A method for generating a searchable small-molecule tandem mass spectrometry library comprising:
    (a) generating, by theoretical calculation and for each of a plurality of small-molecule compounds, a list of ion species, including fragment-ion species that are predicted, by the theoretical calculations, to be generated by tandem mass spectrometry (MS$^n$) analyses, where n≥2;
    (b) comparing at least a subset of the predicted ion species to entries in a database that includes a list of experimentally observed ion species;
    (c) matching a predicted mass-to-charge ratio (m/z) value of each of one or more of the predicted fragment-ion species to a respective experimentally measured m/z value of an experimentally observed fragment-ion species for which information is tabulated in the database;
    d) for each of the one or more said matched predicted m/z values of the predicted fragment-ion species, matching a predicted m/z value of a predicted precursor-ion species that is predicted to yield, upon fragmentation thereof, the predicted fragment-ion species to an experimentally measured m/z value of an experimentally-observed precursor-ion species that is experimentally observed to yield, upon fragmentation, the respective experimentally observed matched fragment-ion species; and
    (e) updating the predicted list of ion species based on information derived from the matches, as determined in step (c), between the predicted and the experimentally measured m/z values.

2. The method as recited in claim 1, wherein the entries in the database pertain to tandem mass spectrometry (MSn) analyses of standard compounds, where n>2.

3. The method as recited in claim 2, further comprising: updating at least one ion species assignment in the database based on information derived from the matches, as determined in step (c), between the predicted and the experimentally measured m/z values.

4. The method as recited in claim 1, wherein the step (a) of generating, by the theoretical calculation and for each of the plurality of small-molecule compounds, the list of predicted fragment-ion species includes consideration of the elements of each said list as being dependent on an adjustable applied fragmentation energy parameter; wherein the step (b) of comparing the at least subset of the predicted ion species to entries in the database comprises comparing said at least subset of the predicted ion species to entries in the database that are tabulated as dependent on an experimentally applied fragmentation energy value; and wherein the step (c) of matching the predicted mass-to-charge ratio (m/z) value of each of one or more of the predicted fragment-ion species to the respective experimentally measured m/z value of the respective experimentally observed fragment-ion species includes matching, within experimental error, values of the fragmentation energy parameter to values of the applied fragmentation energy.

5. The method as recited in claim 1, wherein the matched experimentally measured m/z value is obtained by a mass spectral analysis of a compound that is different than the small-molecule compound for which the respective matched predicted mass-to-charge ratio is calculated.

6. A method for generating a searchable small-molecule tandem mass spectrometry library comprising:
    (a) generating, by theoretical calculation and for each of a plurality of small-molecule compounds, a list of predicted ion species, each said list including a predicted precursor-ion species and a corresponding list of fragment-ion species that are predicted, by the theoretical calculations, to be generated by fragmentation of the respective precursor-ion species;
    (b) comparing at least a subset of the predicted precursor-ion species and the predicted fragment ion species to entries in a database that includes a list of experimentally observed precursor-ion species and that further includes, for each of said experimentally observed precursor-ion species, a list of fragment-ion species that are experimentally observed to be generated by fragmentation of the respective precursor-ion species;

(c) matching a pair of predicted ion species, said pair comprising one of the predicted precursor-ion species and one of the predicted corresponding fragment ion species, to a pair of experimentally observed ion species comprising one of the experimentally observed precursor ion species and its corresponding experimentally observed fragment-ion species;

(d) identifying at least one other predicted fragment-ion species in the list of predicted fragment-ion species corresponding to the matched precursor-ion species for which there is no match in the list of experimentally observed fragment-ion species that correspond to the matched experimentally observed precursor-ion species; and (e) updating the predicted list of ion species by deleting or otherwise marking as invalid an entry or entries in the predicted list of ion species corresponding to the at least one other predicted fragment-ion species.

7. The method as recited in claim 6, wherein the list of predicted ion species further includes, for each small molecule compound, a respective list of fragmentation pathways species that are predicted, by the theoretical calculations, to be generated by tandem mass spectrometry (MSn) analyses, where n>2, from first-generation precursor ions derived from the respective small molecule compound, and wherein the step (e) of updating the list of predicted ion species includes deleting or otherwise marking as invalid all fragmentation pathways that include a fragment-ion species that is predicted to be generated by fragmentation of an ion species that is deleted or otherwise marked as invalid.

8. The method as recited in claim 6, wherein the entries in the database pertain to tandem mass spectrometry (MSn) analyses of standard compounds, where n>2.

9. The method as recited in claim 8, further comprising: updating at least one ion species assignment in the database based on information derived from the matched pairs of ion species.

10. The method as recited in claim 6, wherein the step (a) of generating, by the theoretical calculation and for each of the plurality of small-molecule compounds, the list of predicted fragment-ion species includes consideration of the elements of each said list as being dependent on an adjustable applied fragmentation energy parameter; wherein the step (b) of comparing at least the subset of the predicted fragment ion species to entries in the database comprises comparing said at least subset of the predicted fragment ion species to entries in the database that are tabulated as dependent on an experimentally applied fragmentation energy value; and wherein the step (c) of matching the pair of predicted ion species to the pair of experimentally observed ion species includes matching, within experimental error, values of the fragmentation energy parameter to values of the applied fragmentation energy.

11. The method as recited in claim 6, wherein the matched pair of experimentally observed ion species comprising the experimentally observed precursor ion species and its corresponding experimentally observed fragment-ion species are obtained by a mass spectral analysis of a compound that is different than the small-molecule compound for which the respective matching pair of predicted precursor-ion and fragment ion species was calculated.

12. A method for generating a searchable small-molecule tandem mass spectrometry library comprising:

(a) generating, by theoretical calculation and for each of a plurality of small-molecule compounds, a list of ion species, including fragment-ion species that are predicted, by the theoretical calculations, to be generated by tandem mass spectrometry ($MS^n$) analyses, where n≥2, the list of predicted ion species comprising a tree structure that denotes fragmentation pathways;

(b) comparing at least a subset of the predicted ion species to entries in a database that includes a list of experimentally observed ion species;

(c) matching a predicted mass-to-charge ratio (m/z) value of each of one or more of the predicted fragment-ion species to a respective experimentally measured m/z value of an experimentally observed fragment-ion species for which information is tabulated in the database; and (d) updating the predicted list of ion species based on information derived from the matches, as determined in step (c), between the predicted and the experimentally measured m/z values, wherein the updating comprises one or more of the group consisting of: (i) marking fragmentation pathways of the predicted list of ion species as verified and (ii) deleting or marking as invalid non-observed fragmentation pathways of the predicted list of ion species.

13. The method as recited in claim 12, wherein the entries in the database pertain to tandem mass spectrometry (MSn) analyses of standard compounds, where n>2.

14. The method as recited in claim 13, further comprising: updating at least one ion species assignment in the database based on information derived from the matches, as determined n step (c), between the predicted and the experimentally measured m/z values.

15. The method as recited in claim 12, wherein the step (a) of generating, by the theoretical calculation and for each of the plurality of small-molecule compounds, the list of predicted fragment-ion species includes consideration of the elements of each said list as being dependent on an adjustable applied fragmentation energy parameter; wherein the step (b) of comparing the at least subset of the predicted on species to entries in the database comprises comparing said at least subset of the predicted ion species to entries ire the database that are tabulated as dependent on an experimentally applied fragmentation energy value; and wherein the step (c) of matching the predicted mass-to-charge ratio (m/z) value of each of one or more of the predicted fragment-ion species to the respective experimentally measured m/z value of the respective experimentally observed fragment-ion species includes matching, within experimental error, values of the fragmentation energy parameter to values of the applied fragmentation energy.

16. The method as recited in claim 12, wherein the matched experimentally measured m/z value is obtained by a mass spectral analysis of a compound that is different than the small-molecule compound for which the respective matched predicted mass-to-charge ratio is calculated.

17. The method as recited in claim 12, wherein the small-molecule compounds are metabolites.

18. The method as recited in claim 1, wherein the small-molecule compounds are metabolites.

19. The method as recited in claim 6, wherein the small-molecule compounds are metabolites.

\* \* \* \* \*